United States Patent [19]

Brockway

[11] Patent Number: 4,853,215

[45] Date of Patent: Aug. 1, 1989

[54] TREATMENT OF HAIR

[75] Inventor: Barbars E. Brockway, Berkshire, England

[73] Assignee: University of Reading of Whiteknights House, Reading, England

[21] Appl. No.: 116,297

[22] Filed: Nov. 4, 1987

[30] Foreign Application Priority Data

Nov. 4, 1986 [GB] United Kingdom ............... 8626356

[51] Int. Cl.⁴ .......................... A61K 7/09; A45D 7/02
[52] U.S. Cl. ....................................... 424/71; 132/206
[58] Field of Search .............. 435/233; 424/71; 132/7, 132/206

[56] References Cited

PUBLICATIONS

Chemical Abstracts, vol. 100, No. 13, 3/26/84, p. 264, (Freedman et al.), "Properties of Protein Disulphide–Isomerase".
Chemical Abstracts, vol. 104, No. 1, (Kaderbhai et al.), "Studies on the Formation of Intrachain Disulphide in Newly Biosynthesized Bovine Prolactin, Role of Protein Disulphide Isomerase".
Chemical Abstracts, vol. 86, No. 15, (Grynberg et al.), "Occurrence of a Protein–Disulphide Isomerase in Wheat Germ".
Chemical Abstracts, vol. 94, No. 5, (Creighton et al.), "Catalysis by Protein–Disulphide Isomerase of the Unfolding and Refolding of Proteins with Disulphide Bonds".
Freedman et al., "Properties of Protein Disulfide–Isomerase", Physiological, Toxicological, and Clinical Aspects, edited by A. Larson, et al., Raven Press, New York, 1983, pp. 273–283.
Kaderbhai et al., "Studies on the Formation of Intrachain Disulfide Bonds in Newly Biosynthesized Bovine Prolactin, Role of Protein–Disulfide Isomerase", Eur. J. Biochem., 1985, 153(1), 167–178.
Creighton et al., "Catalysis by Protein–Disulfide Isomerase of the Unfolding and Refolding of Proteins with Disulfide Bonds", J. Mol. Biol., 1980, 142(1), 43–62.

Primary Examiner—Ellis P. Robinson
Assistant Examiner—Susan S. Rucker
Attorney, Agent, or Firm—Larson and Taylor

[57] ABSTRACT

Hair is reconfigured by treatment with a composition comprising an enzyme (protein disulphide isomerase) and a cofactor therefor.

9 Claims, No Drawings

TREATMENT OF HAIR

BACKGROUND OF THE INVENTION

The present invention relates to a process for treating hair; and to a composition for use in such treatment. It is particularly applicable to the styling of human hair, e.g. by 'permanent waving'.

It has long been known that hair consists largely of protein ('keratin') and that its physical form is affected by the arrangement of disulphide linkages between cysteine residues. Thus known hair treatment compositions employ thiols which are believed to undergo redox reactions so that the keratin disulphide linkages are unmade and remade, allowing the hair to be given a new configuration during the process. However, the thiols are disagreeable, even dangerous, compounds and the compositions generally need to be strongly alkaline. They are unpleasant to use, and can harm the skin and hair.

SUMMARY OF THE INVENTION

Broadly the present invention is based on the discovery that certain enzymes and enzyme preparations can be used to treat hair safely, under very mild conditions. They can thus be used to alter its configuration, e.g. for curling, waving or straightening.

In one aspect the invention provides a process for treating hair in which the hair is reconfigured while being contacted with a composition which comprises an aqueous medium containing a protein disulphide isomerase, under conditions such that the enzyme can catalyse rearrangement of disulphide linkages in the hair. Generally the composition will contain a cofactor for the enzyme.

An isomerase is preferably to (for example) a reductase since the latter requires the presence of a hydrogen donor such as NADPH. However for some purposes other types of enzyme may be useful.

Preferably the composition contains substantial amounts of only one enzyme.

In a second aspect the invention provides an enzyme-containing composition for use in such a process. The composition may be usable directly or, more usually, after one or more preliminary steps such as dilution, solution or admixture. A composition may comprise a stable enzyme preparation comprising an enzyme and a carrier (which may be water, generally including a buffer; and/or may be a (preferably soluble) solid).

DESCRIPTION OF THE PREFERRED EMBODIMENTS

A suitable type of enzyme is the protein disulphide isomerase E.C.5.3.4.1, hereafter referred to as PDI. This enzyme is well-characterised and is commercially available from GENZYME (Genzyme Biochemicals Ltd., Maidstone, England; Genzyme Corp., Boston, Mass., U.S.A.). It has been described by N. Lambert and R. B. Freedman (1983 Biochem. J. 213 225-234). This type of enzyme seems to occur in every eukaryotic tissue which synthesises a secreted protein. The most easily obtainable tissue type is bovine liver PDI. This may be isolated as follows.

500 g of diced bovine liver is washed with physiological saline and extracted at neutral pH with phosphate buffer which contains 1% Triton. This gives an enzyme extract which is then concentrated and purified by procedures involving heat treatment, ammonium sulphate precipitation, ion exchange chromatography, dialysis and finally lyophilization. (See the paper by Lambert and Freedman for fuller details.)

A purer enzyme may be prepared by genetic engineering, i.e. using cloned DNA in a suitable culture.

For use, it is generally necessary to add a very small amount of a low molecular weight thiol as a cofactor. (The concentration need only be of the order of micromolar.)

Suitable thiols which are readily available and are acceptable for in vivo treatment of human hair include cysteine and reduced glutathione.

A suitable composition for use contains 0.03 to 1.5 g (and preferably 0.5 to 1.5 g) of PDI and 1 to 1000 (and preferably 10 to 1000) micromoles of a cofactor per liter, buffered to a pH in the range 7-8, and preferably pH 7.5, suitably with a phosphate buffer. It may also contain other components, e.g. selected from wetting agents, perfumes, and carriers. Since the thiol is susceptible to aerial oxidation, the storage form of the composition should provide protection from air. The enzyme and cofactor are preferably stored separately as freeze dried powders. The cofactor component thereof, may include the phosphate buffer and any other components, and be stored in an air-free vessel, e.g. a foil sachet, possible under nitrogen, and/or in an encapsulated form. The enzyme should be protected from harmful materials, e.g. by being packaged analogously to the cofactor. For use, a sachet of cofactor and phosphate buffer is opened and the contents are dissolved in water, preferably at 28° C. Then the enzyme is added.

Hair is treated at a temperature slightly above room temperature, e.g. 25° to 40° C., preferably 25° to 32° C., for a period of up to 1 hour.

The PDI may be modified to improve its stability or effectiveness. Thus it may be dissociated into its sub-units, which can show greater activity (presumably since the active sites are then more accessible, particularly to bulky substrates such as keratin, than in the whole enzyme). The enzyme (which term includes a dissociated subunit of natural PDI) may be immobilised on a carrier. A suitable carrier has a large surface area, since an insoluble substrate such as keratin cannot penetrate into the interior. Thus we may use polystyrene beads or other carriers of synthetic polymers (such as polyvinyl resins, nylon, and isocyanate-capped polyurethane foam). This can improve stability and aid storage and use. A carrier may be given a convenient shape, e.g. forming at least part of a hair roller.

The enzyme may be chemically modified to alter its binding properties and Km value.

An example of the use of a composition according to the invention follows.

EXAMPLE

A subject's hair was washed with a conventional shampoo and rinsed. The wet hair was wound tightly on curling rollers of diameter 0.5 cm, and a solution of the following composition at a temperature of 28° C. was applied:
 PDI (Genzyme . . . ) 1 g/l
 Reduced glutathione (SIGMA) 1 mM
 50 mM Phosphate buffer to pH 7.5
 Distilled water.

The hair was kept warm (25°-32°) for 45 minutes, then the rollers were removed and the hair was washed free of the composition. After conventional drying, it was found to be well curled, comparable to the result of treatment with a conventional waving lotion.

I claim:

1. A process for treating hair in which the hair is urged to undergo macroscopic reconfiguration while being contacted with a composition which is safe for topical application to a living human subject, wherein said composition comprises an aqueous medium containing protein disulphide isomerase E.C.5.3.4.1, under conditions such that the enzyme can catalyse rearrangement of disulphide linkages in the hair.

2. A process according to claim 1 in which the composition contains 0.5 to 1.5 g of protein disulphide isomerase per liter.

3. A process according to claim 1 in which the composition contains a thiol which serves as a cofactor for the enzyme.

4. A process according to claim 3 in which the cofactor is selected from cysteine and reduced glutathione.

5. A process according to claim 3 in which there are 10 to 1000 micromoles of cofactor per liter.

6. A process according to claim 1 wherein the composition is in the temperature range 25° to 32° C.

7. A composition for use in treating hair to facilitate changing its macroscopic configuration, the composition being safe for topical application to a living human subject and comprising protein disulphide isomerase E.C.5.3.4.1 a thiol which serves as a cofactor therefor, and at least one material selected from buffers, carriers, perfumes and wetting agents.

8. A composition according to claim 7 adapted to produce on addition of water a solution containing 0.5 to 1.5 g of protein disulphide isomerase and 10 to 1000 micromoles of cofactor per liter.

9. A composition according to claim 7 wherein the cofactor is selected from cysteine and reduced glutathione.

* * * * *

UNITED STATES PATENT AND TRADEMARK OFFICE
CERTIFICATE OF CORRECTION

PATENT NO. : 4,853,215
DATED : August 1, 1989
INVENTOR(S) : BROCKWAY, Barbara E.

It is certified that error appears in the above-identified patent and that said Letters Patent is hereby corrected as shown below:

Title page, item [75] should read as follows:

-- [75] Inventor: Barbara E. Brockway, Berkshire, England --

Signed and Sealed this

Nineteenth Day of June, 1990

Attest:

HARRY F. MANBECK, JR.

*Attesting Officer*   *Commissioner of Patents and Trademarks*